(12) United States Patent
Zadesky et al.

(10) Patent No.: US 10,603,690 B2
(45) Date of Patent: Mar. 31, 2020

(54) PORTABLE ELECTRONIC DEVICE USING A TACTILE VIBRATOR

(71) Applicant: Apple Inc., Cupertino, CA (US)

(72) Inventors: Stephen P. Zadesky, Cupertino, CA (US); Fletcher R. Rothkopf, Cupertino, CA (US); Stephen B. Lynch, Cupertino, CA (US); Martin Auclair, Waterloo (CA)

(73) Assignee: Apple Inc., Cupertino, CA (US)

( * ) Notice: Subject to any disclaimer, the term of this patent is extended or adjusted under 35 U.S.C. 154(b) by 1006 days.

(21) Appl. No.: 14/774,503

(22) PCT Filed: Mar. 3, 2014

(86) PCT No.: PCT/US2014/019936
§ 371 (c)(1),
(2) Date: Sep. 10, 2015

(87) PCT Pub. No.: WO2014/164018
PCT Pub. Date: Oct. 9, 2014

(65) Prior Publication Data
US 2016/0023245 A1   Jan. 28, 2016

Related U.S. Application Data

(60) Provisional application No. 61/776,676, filed on Mar. 11, 2013.

(51) Int. Cl.
| | | |
|---|---|---|
| A61B 5/024 | (2006.01) | |
| H01L 41/08 | (2006.01) | |
| G10K 9/122 | (2006.01) | |
| G06F 1/16 | (2006.01) | |
| B06B 1/06 | (2006.01) | |
| G06F 3/01 | (2006.01) | |

(Continued)

(52) U.S. Cl.
CPC ........ *B06B 1/0603* (2013.01); *A61B 5/02133* (2013.01); *A61B 5/02438* (2013.01);
(Continued)

(58) Field of Classification Search
CPC . H01L 41/08; H01L 41/0933; H01L 41/0973; H01L 41/0986
See application file for complete search history.

(56) References Cited

U.S. PATENT DOCUMENTS

| | | |
|---|---|---|
| 7,503,989 B2 | 3/2009 | Picciotto et al. |
| 7,860,259 B2 | 12/2010 | Onishi et al. |

(Continued)

FOREIGN PATENT DOCUMENTS

| | | |
|---|---|---|
| CN | 1926917 | 3/2007 |
| CN | 101427393 | 5/2009 |

(Continued)

*Primary Examiner* — Thomas M Dougherty
*Assistant Examiner* — Karen B Addison
(74) *Attorney, Agent, or Firm* — Brownstein Hyatt Farber Schreck, LLP

(57) ABSTRACT

Examples of portable electronic devices including a piezo actuated vibrator for providing tactile feedback to the user are described. Portable electronic devices according to the present disclosure may include tactile feedback devices, which may be driven by a piezoelectric actuator/vibrator that is operatively coupled to or embedded into the housing of a portable electronic device. In some examples, the housing of the electronic device itself can be made of piezoelectric ceramic material. The piezoelectric element may be coupled to the housing of the product to cause the housing to deflect and/or vibrate. In some examples, the housing of the portable electronic device, which may be a portable media player device, may be configured for placement directly or indirectly in contact with the user's skin such that vibrations of the housing may be felt directly (without audible feedback) by the user.

21 Claims, 8 Drawing Sheets

(51) Int. Cl.
*H01L 41/09* (2006.01)
*A61B 5/021* (2006.01)
*A61B 5/00* (2006.01)

(52) U.S. Cl.
CPC ........ *A61B 5/02444* (2013.01); *A61B 5/7455* (2013.01); *B06B 1/06* (2013.01); *G06F 1/163* (2013.01); *G06F 3/016* (2013.01); *G10K 9/122* (2013.01); *H01L 41/08* (2013.01); *H01L 41/0933* (2013.01); *H01L 41/0973* (2013.01); *H01L 41/0986* (2013.01); *A61B 5/7405* (2013.01)

(56) References Cited

U.S. PATENT DOCUMENTS

| | | | |
|---|---|---|---|
| 8,436,825 B2 | 5/2013 | Coni et al. | |
| 8,717,151 B2 * | 5/2014 | Forutanpour | G06F 3/04847 340/407.1 |
| 9,054,605 B2 | 6/2015 | Jung et al. | |
| 9,246,551 B2 | 1/2016 | Yeo et al. | |
| 2007/0177747 A1 * | 8/2007 | Onishi | H04R 17/00 381/190 |
| 2012/0286944 A1 * | 11/2012 | Forutanpour | G06F 3/016 340/407.1 |
| 2014/0043053 A1 | 2/2014 | Huber et al. | |
| 2015/0318100 A1 | 11/2015 | Rothkopf et al. | |

FOREIGN PATENT DOCUMENTS

| | | | | |
|---|---|---|---|---|
| CN | 102460938 | | 5/2012 | |
| CN | 102648860 | | 8/2012 | |
| JP | 2000-269563 | * | 9/2000 | ............. H01L 41/08 |
| JP | 2000269563 | | 9/2000 | |
| KR | 1020050038645 | | 4/2005 | |
| KR | 20130005715 | | 1/2013 | |
| WO | WO2012/169138 | | 12/2012 | |

* cited by examiner

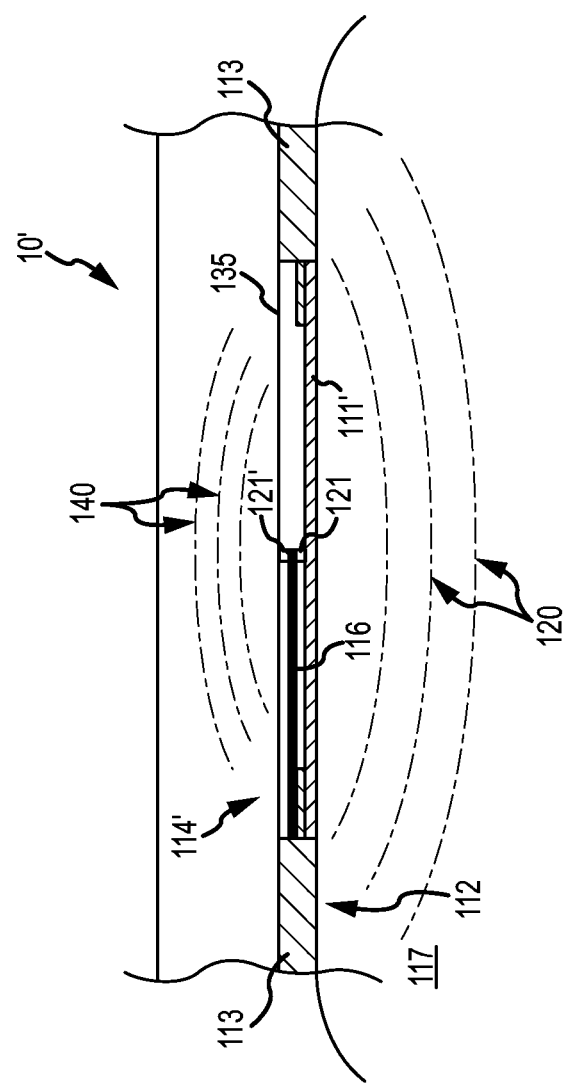

PORTABLE ELECTRONIC DEVICE USING A TACTILE VIBRATOR

CROSS-REFERENCE TO RELATED APPLICATIONS

This application is a 35 U.S.C. § 371 application of PCT/US2014/019936, filed Mar. 3, 2014 and titled "Portable Electronic device Using a Tactile Vibrator," which is a nonprovisional of and claims priority to U.S. Provisional Patent Application No. 61/776,676, filed Mar. 11, 2013 and titled "Portable Electronic Device Using a Tactile Vibrator," the disclosures of which are hereby incorporated by reference herein in their entireties.

TECHNICAL FIELD

The present disclosure relates generally to portable electronic devices and more specifically to electronic devices adapted for placement against the user's skin (directly or indirectly) and configured to provide tactile feedback to the user.

BACKGROUND

Portable electronic devices, such as personal data assistants, media players, mobile telephones, tablet computers, and other similar computing devices have become ubiquitous in our daily lives. In some instances, the user may desire to interact with the portable device and/or receive feedback or alerts from the device. Frequently feedback may be audible and/or may consequently be perceived as a nuisance or even yet may fail to preserve the privacy of the communication between the user and his portable electronic device. For example, the user may wish to receive an alert at a particular time or upon the occurrence of a particular even, however the user may wish the alert to be entirely private (e.g., imperceptible by others in the user's surroundings). Non-audible or vibrate modes of operation of certain devices may generally be known, however even these modes have a residual sound effect which may be perceived by the user or persons near the user. Typical vibrators of portable electronics use the spinning of an unbalanced motor to generate vibration, however vibration produced in this manner is typically more aggressive than may be necessary and may consequently be more noticeable and/or audible.

SUMMARY

Portable electronic devices including piezo actuated vibrators (also referred to herein as vibrator assemblies) for generating tactile and/or audible alerts are described. According to some examples, the portable electronic device may include a housing and a vibrator assembly. The vibrator assembly may include a diaphragm coupled to the housing, and a piezoelectric element (also referred to herein as piezoelectric actuator or a piezoelectric transducer) coupled to the housing and the diaphragm and configured to cause the diaphragm to vibrate. The piezoelectric element may be spaced apart from the diaphragm with a cavity defined between the piezoelectric element and an interior surface of the diaphragm. In some embodiments, the piezoelectric element may be coupled to the diaphragm using at least one connector attached to one or more ends of the piezoelectric element.

Portable electronic devices according to the present disclosure may be configured to be worn by a user, for example by being attached to a body part of a user. In this regard, the portable electronic device may include an attachment mechanism, for example a strap, a clip or a band, for securing the portable electronic device to the body part of the user. The vibrator assemblies described may be configured to generate vibrations which may be perceived tactually (e.g., in the form of tactile feedback) and/or audibly (e.g., in the form of sound) by the user. In certain examples, the vibrator assembly may be configured to generate audible vibrations in addition to or instead of the tactile feedback. In other examples, the portable electronic device may further include a sound generating component configured to provide a noise cancellation signal for reducing or canceling out sound generated by the vibrator assembly. The noise cancellation functionality may be incorporated within the vibrator assembly. For example, the noise cancellation function may be provided by a sound generating diaphragm of the vibrator assembly, which may be operatively coupled to circuitry (e.g., inverse waveform generator) to produce the noise cancellation signal. In certain examples, the vibrator assembly of the portable electronic device may be further configured to detect movement of the user or the user's skin, for example for detecting a pulse or a heartbeat of the user. The vibrator assembly may be integrated with existing design features of the portable electronic device. In this regard, the diaphragm may have a shape corresponding to a shape of an existing feature of the housing. For example, the diaphragm may have a shape corresponding to a trim feature or corresponding to the shape of a logo affixed to or embedded in the housing.

According to examples of the present disclosure, a vibrator assembly including a dual diaphragm configuration may be implemented. The vibrator assembly may include a first diaphragm coupled to the housing and a second diaphragm opposite and spaced apart from the first diaphragm. The vibrator assembly may further include a piezoelectric element spaced apart from and coupled to the first and second diaphragms and configured to cause the first and second diaphragms to vibrate simultaneously. Portable electronic devices according to the examples herein may be adapted to be worn by a user and may include a housing made from a ceramic material, at least of portion of said ceramic material being a piezoceramic material. The piezoceramic material in the housing may be operatively coupled to circuitry enclosed within the housing and may be configured to drive the piezoceramic material to cause a portion of the housing to deflect. In some examples, the housing of the portable electronic device may include a curved exterior surface. The curved surface may be convex, concave, or have other shape configured to fit conformally against a user's skin (directly or indirectly). In some examples, portable electronic devices according to the present disclosure may include a housing which includes an interior surface and an exterior surface, and wherein at least a portion of the housing includes a piezoelectric material embedded between the interior and exterior surfaces of the housing. The piezoelectric material may be arranged such that its axis of elongation is perpendicular to at least one of the interior surface or the exterior surface of the housing.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, as described below.

FIG. 5 is a schematic illustration of a piezo actuated vibrator according to another example of the present disclosure.

DETAILED DESCRIPTION OF PREFERRED EMBODIMENTS

Figure 1:
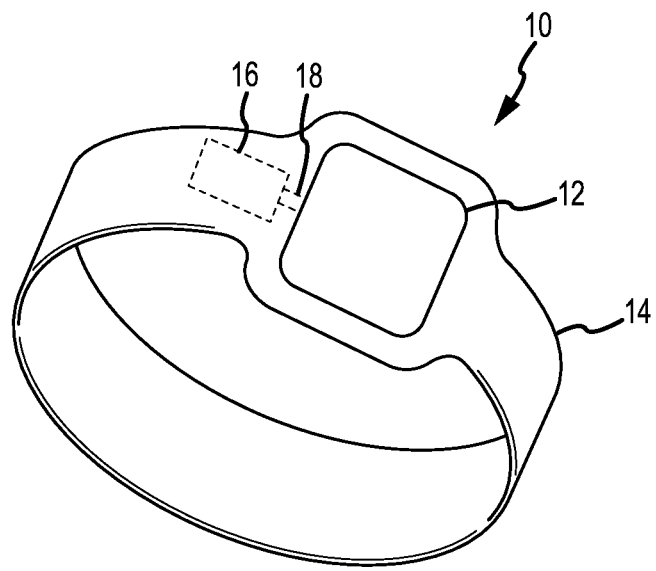
FIG. 1 is an illustration of an example portable electronic device according to one example of the present disclosure.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are implicitly contemplated herein.

Figure 2:
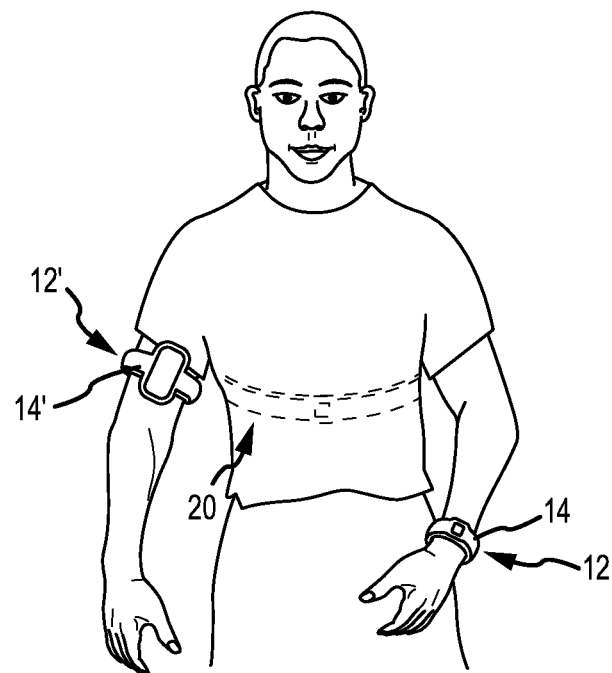
FIG. 2 is an illustration of sample portable electronic devices in use according to examples of the present disclosure.

The present disclosure relates to portable electronic devices including one or more vibration generating systems (also referred to herein as vibrators or vibration assemblies), which may be configured to generate audible and/or inaudible vibrations. The present disclosure may be applicable to virtually any consumer electronic product which is designed to come into contact with the user's skin, including devices which are held by the user, attached to a body part of the user or otherwise placed against the user's skin. The product need not come in direct contact with the user's skin as it may be configured to provide tactile feedback through clothing. FIGS. 1-3 show illustrations of several examples of portable electronic devices according to the present disclosure. According to one example, the portable electronic device 10 may be a media player 12 or a timekeeping device (e.g., a digital watch or a timer), or any other wearable device or item. The portable electronic device 10 may include a mechanism for attachment of the device 10 to the user, such that the device 10 is in contact with the user's skin, whether directly or indirectly (e.g., through clothing). The mechanism for attachment may be a strap 14, for example, for affixing the device 10 to the user's wrist, forearm, or upper arm. For example, and as shown in FIG. 2, the portable electronic device may be a media player 12' or other dedicated or multifunctional computing device which may be secured against the user's skin by a band or other elastic or flexible member. The arm band 14' may be integral with the portable electronic device or it may be removable. In other instances, one or more straps may be included for attaching a tablet or eBook reader (not shown) to a person's palm or against a person's forearm, or other body part. Other mechanisms may include clips, loops, bands, or the like. Removable adhesives may be used, for example to attach a flexible patch comprising circuitry programmed with a desired functionality against the user's skin. In yet other examples, the portable electronic device 10 may be or include a biometric monitor 20 (one example of which is shown in FIG. 2), such as a heart rate monitor. In such examples, the portable electronic device may be configured for placement against the chest or other body parts of the user suitable for monitoring heart rate or pulse of the user.

Referring back to FIG. 1, portable electronic devices according to the present disclosure (e.g., devices 12, 12', 20, as examples) may include a piezo actuated vibrator 16, which may be mounted to or incorporated within the housing of the electronic device, as will be described in further detail below. The piezo actuated vibrator 16 may be operatively coupled to circuitry 18 of the portable electronic device 10 in order to drive the piezo actuated vibrator 16, as may be desired or required by functionality of the device. For example, the piezo actuated vibrator 16 may be driven to vibrate at a predetermined time or in response to the occurrence of a certain event (examples of which include receipt of an email, text message alert, push notification and so on) to generate an auditory and/or tactile alert. For example, the piezoelectric material may be configured to stimulate one or more diaphragms that produce noise or inaudible vibrations. In some examples, active noise cancellation may also be used to reduce or cancel out any sound produced by the piezoelectric vibrator. Other potential uses for the auditory or tactile alerts may include sport performance indicators, calendar notification, heptic feedback, conditioning, reminders, phone ringers, and others. The piezo actuated vibrator 16 may be configured to generate audible sound and/or inaudible vibrations (also referred to herein as tactile vibrations or tactile stimulation) through or by vibrating the housing of the device 10, as will be further described.

Figure 3B:
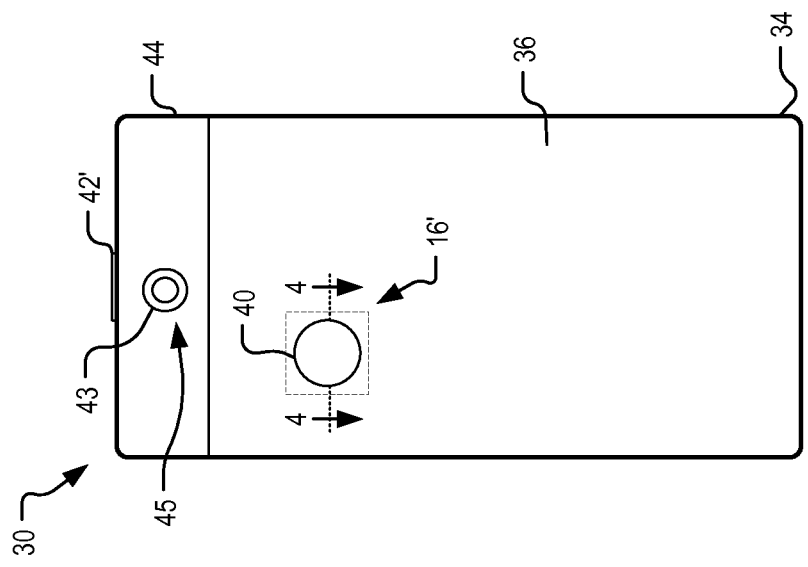
FIGS. 3A and 3B are front and back views (respectively) of a portable electronic device according to another example of the present disclosure.
Figure 3A:
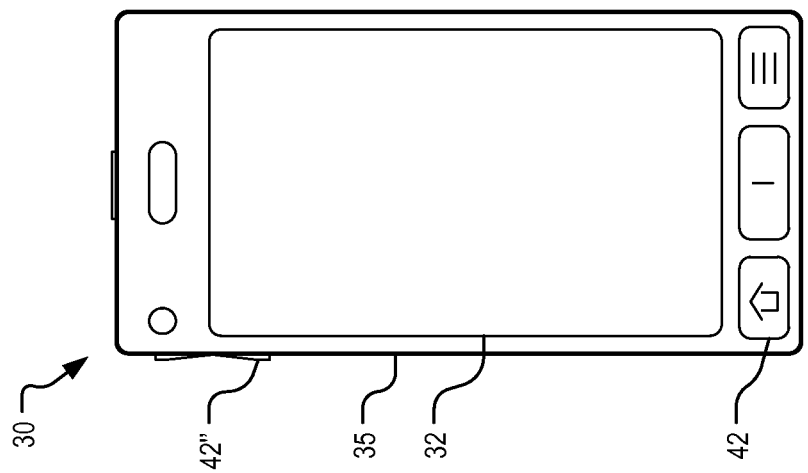

FIGS. 3A-3B shows yet another example of a portable electronic device according to the present disclosure. The portable electronic device may be a smart phone 30, which may include a display device 32 (e.g., an LCD, LED, or the like), a housing 34, and circuitry (not shown) enclosed therein. The housing 34 may have virtually any form factor, examples of which include rectangular, circular, elliptical or an irregular shape. Surfaces of the housing 34 may be generally flat or curved. In the present example, the housing 34 may include a back portion 36 which is flat. However, in other examples, the back portion 36 may be curved or otherwise shaped to substantially conform to the body part of the user to which the portable electronic device 10 is to be attached. For, example, the piezo actuated vibrator may be configured to vibrate a portion of the housing (curved or otherwise) to provide tactile feedback to a wearer. The housing may be curved to improve the response of the tactile vibrator. In some examples, the vibrator may be arranged at a location of greatest curvature, which may improve sensitivity to the tactile feedback. Furthermore, the vibration frequency of the vibrator may be tuned to a resonant frequency of the product in order to maximize or otherwise enhance the vibrations felt by the user.

Piezo actuated vibrators according to the present disclosure (e.g., vibrator assembly 16' shown in phantom in FIG. 3B) may be incorporated into or integrated with existing features of the housing. As some examples, such vibrators may be integrated with a logo 40, one or more control buttons 42, 42', 42", trim 44, and other features. In some examples, the piezo actuated vibrator may be integrated within the trim 43 (e.g., portion of the housing) of the camera 45. In yet other examples, the piezo actuated vibrator may be incorporated in a perimeter portion 35 of the housing. Other variations may be used in various embodiments. For the purposes of illustration, several embodiments of piezo actuated vibrators 16' will be further described with references to the schematic illustrations in FIGS. 4-7. As will be understood upon reading, FIGS. 4-7 are provided for illustration purposes only, and thus the components may not be shown to scale. Likewise, for clarity, certain components of the assemblies which are not essential for understanding the examples therein may have been omitted from the figures. While specific examples depicting a single piezo actuator may be depicted, it will be understood that multiple piezo actuators may be used in other examples, or other variations may be implemented as may be appreciated by those skilled in the art.

Figure 4:
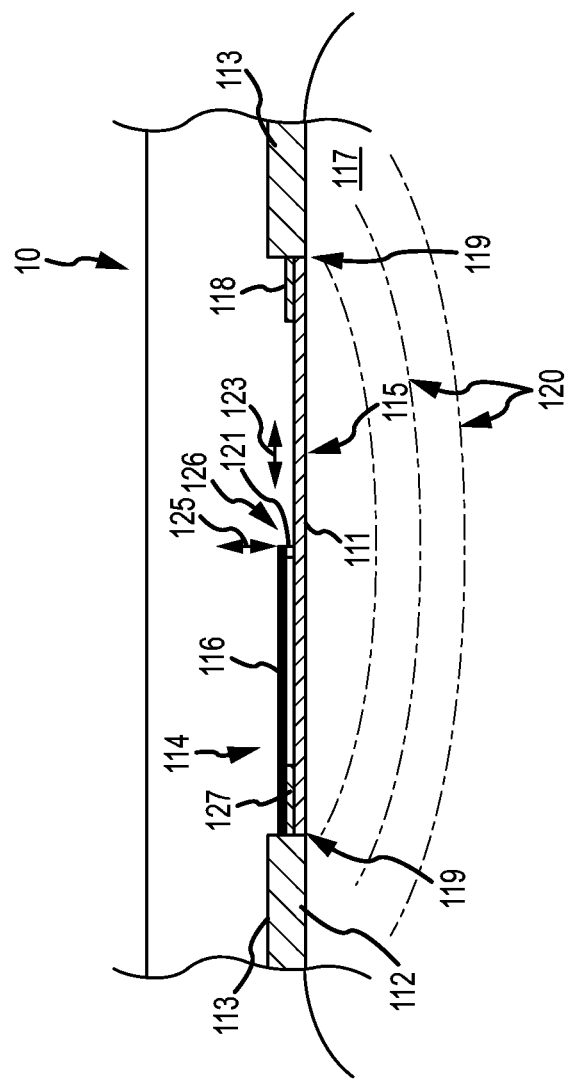
FIG. 4 is a schematic illustration of a piezo actuated vibrator according to one example of the present disclosure.

FIG. 4 shows an example of a piezo actuated vibrator according to one example of the present disclosure. As shown schematically in the example of FIG. 4, the electronic device 10 may include a housing 112 and a piezo actuated vibrator 114, which may include a piezoelectric element 116. In some examples, the housing 112 may include a diaphragm 111 which may be thinner than peripheral portions 113 of the housing around or adjacent to the diaphragm. The diaphragm 111 may be coupled to the housing such that a continuous surface is defined by the diaphragm and housing at the outer surface 115 (also referred to herein as contact surface 115) of the device, including across the boundary 119 of the diaphragm. Joints between the diaphragm and housing may be enforced with a reinforcement member 118, for example to prevent damage at the joint which may be caused by repetitive flexing of the diaphragm (e.g., when the diaphragm is vibrated).

Figure 7:
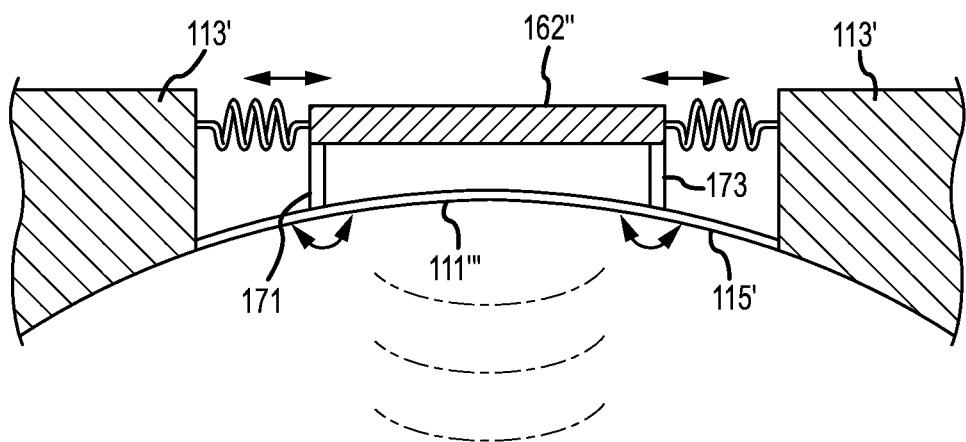
FIG. 7 is a schematic illustration of a piezo actuated vibrator according to yet another example of the present disclosure.
Figure 8:
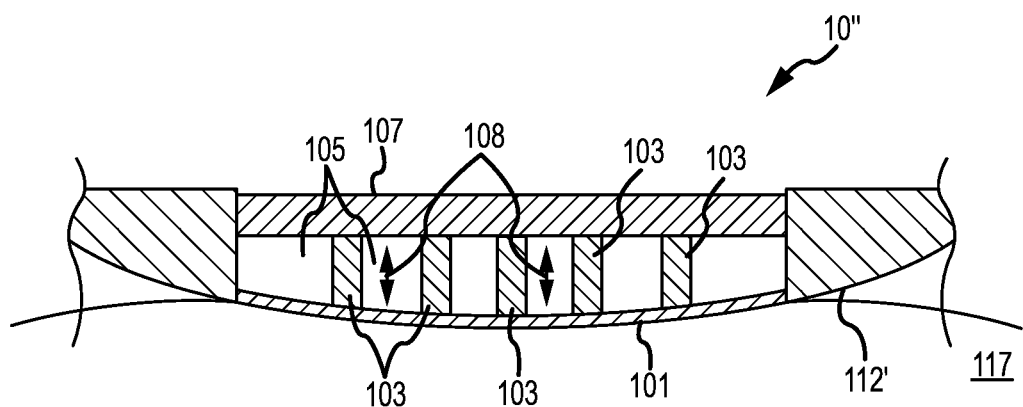
FIG. 8 is a further example of a piezo actuated diaphragm according to examples of the present disclosure.

The electronic device may be configured such that the exterior or contact surface 115 is adapted for placement against the user's skin. In the context of this disclosure, "in contact with the skin" is meant to include direct and indirect contact (e.g., through clothing) of the exterior surface 115 with the skin 117 of a user. As described herein, the electronic device may be configured to be worn by the user and may include a strap or other attachment mechanism (see FIGS. 1-2) adapted for securing the device 10 against a body part of the user. The electronic device may be a portable media player, a smartphone, or other mobile computing device. In some examples, the electronic device may be a time keeper, a heart rate monitor, or any other biometric monitoring device or may be a mobile computing device including functionality adapted for biometric monitoring. In the schematic illustration in FIG. 1, the housing 112 and diaphragm 111 is depicted as having a flat continuous surface, however, in some examples, the housing 112 of the electronic device 10 may be curved (e.g., as shown in FIGS. 7 and 8) and or otherwise adapted to fit conformally against a body part of the user, such as the wrist, forearm, upper arm, chest, neck, ankle, or others. In some examples, using a curved surface may enhance the sensitivity and/or responsiveness of the device as described herein and appreciated by those skilled in the art.

In certain examples, the electronic device 10 may be configured to be worn with the contact surface adjacent to or against the user's skin, or adjacent to clothing through which a haptic output from the device may still be sensed by the user. When worn (e.g., when strapped to the user's arm or wrist), the flat surface may compress a portion of the user's skin surface thus creating a better contact and enhancing the sensitivity to the tactile vibrations (e.g., as indicated by vibration waves 120) generated by the device. In other examples, the housing 113 may be configured such that it is spaced apart from the user's skin, for example to provide an air gap between the skin and the diaphragm for better sound generation (see e.g., FIG. 9). External structures, such as rounded spacers or nubs may be included at the exterior of the housing, for example around a perimeter of the diaphragm or at a perimeter of the back portion of the housing for maintaining the air gap. The rounded spacer may provide the housing in a spaced apart position relative to the body part of the user. In certain examples, one or more tactile vibrators may be built into the foot portions of the spacers, while an audio vibrator is located between the spacers.

In some examples, and as shown in FIG. 4, the piezo actuated vibrator 114 may include a single piezo actuated diaphragm 111. The diaphragm 111 may be coupled to a piezoelectric element 116 such that the diaphragm may be driven to vibrate using the piezoelectric element 116. In this regard, the piezoelectric element 116 may be configured as a piezoelectric actuator. The piezoelectric element (e.g., piezoelectric actuator) may include piezoelectric material. Generally, a piezoelectric material (also referred to herein as piezo material) is a material which produces a voltage in response to an applied force, typically, but not limited to, a uniaxial compressive force. Conversely, a change in dimensions can be induced by the application of a voltage to a piezoelectric material. It is in this converse mode of operation that piezoelectric material may function as a piezoelectric actuator. Examples of piezoelectric materials include quartz, barium titanate, lead niobate, lead zirconate titanate (also known as PZT), and polyvinylidene fluoride, to name a few. A wide range of piezoelectric transducers may be implemented according to the present disclosure, examples of some of which are described herein. As will be understood, the particular examples described are illustrative in nature and the scope of the present disclosure is not limited to the specific examples described herein.

Piezoelectric materials may be incorporated and/or configured into a variety of piezoelectric transducers which may function as motors (e.g., piezoelectric actuators) and/or generators (e.g., piezoelectric sensors). Piezoelectric actuators according to the present disclosure may be linear actuators, sheet actuators, and/or bending actuators.

For example, the piezoelectric material may be provided as a singe sheet or bar of piezo material (e.g., PZT), which can be energized to produce motion in the thickness, length, and/or width directions of the sheet or bar, depending on the polarity of the particular material used. Thus, the piezo sheet or bar may be stretched or compressed by the application of voltage, or conversely may generate voltage by mechanically stretching or compressing the piezo sheet or bar. Such unilayer configuration is typically referred to as a linear actuator because it acts along a linear direction (e.g., expansion along the length, thickness or width of the material).

According to other examples, the piezoelectric actuator may be configured as a bender. A sheet, which may range anywhere from about 0.005 inches to about 0.1 inches, or a bar of piezo material may be adhered along its length to a non-piezo substrate or backing material. In this manner, when voltage is applied to the piezo material causing it to contract or expand, the non-piezo material may bend due to the resulting change of dimension of the piezo material.

One limitation of certain piezo actuators is the size of the stroke of the actuator (e.g., the amount of deflection it may be able to generate). In some examples, the stroke of a piezoelectric actuator may be increased by stacking two or more layers of piezo material as will be described. A multi-layer piezoelectric element may be obtained by adhering two or more sheets of piezo to create a stack along the thickness of the piezo material. The polarities of each sheet may be selected to increase the bend of the piezo actuator. This type of stack may be referred to as a "bender" because it may be capable of achieving larger deflections that a single layer transducer. In other examples, a multi-layer stack may be achieved along the longitudinal direction (e.g., by arranging and coupling bars of piezo material along their lengths). This type of stack may be referred to as "extenders" and may be stiffer and produce less deflection than a single bar of piezo material of equivalent length, but may be capable of producing higher forces. Other examples to modify the stroke of the actuator may be determined based on the manner of coupling the piezo actuator to the remaining structure and/or by using certain features (e.g., a lever arm, or flexural arrangements) to achieved mechanical advantage, as will be further described.

Referring to the example in FIG. 4, the piezoelectric element 116 may be spaced apart from the diaphragm 111 (e.g., using spacer 127) and may be coupled to the diaphragm using a connector 121. The piezoelectric element 116 may be cantilevered off one side of the housing and the free end 126 of the piezoelectric element 116 may be coupled to a central portion of the diaphragm 111 using connector 121. In other examples, the piezoelectric element may be positioned adjacent to the interior surface of the diaphragm 111 and attached thereto. The piezoelectric element 116 and/or connector 121 may be attached to the diaphragm using conventional techniques, for example by adhering, soldering, or brazing the components together.

The piezoelectric element 116 may be configured according to any of the examples of piezoelectric transducer described herein or appreciated by those skilled in the art. For example, the piezoelectric element 116 may be a bar of PZT which is configured as a liner actuator (e.g., extending or contracting along direction indicated by arrow 123). As will be understood, an extension or contraction of the piezoelectric element 116 along a particular direction 123 may result in a downward or upward deflection of the diaphragm 111 by virtue of the coupling between the piezoelectric element 116 and the diaphragm 111. In some examples, the piezoelectric element 116 may be configured as a bender adapted to deflect up and down (e.g., along the direction indicated by arrow 125). Up and down vibrations of the piezoelectric element 116 may cause corresponding up and down vibrations of the diaphragm 111, albeit by virtue of a out-of-plane load to the diaphragm through the connector 121. Other coupling arrangements may be used.

In other examples, the piezo actuated vibrator 114 may be configured to function as a microphone transducer. In one mode of operation, the piezo actuated vibrator 114 may be configured to generate sound when driven to particular frequencies. In a converse mode, the piezo actuated vibrator 114 may be configured to transduce mechanical energy to electrical power. In this regard the piezo actuated vibrator 114 may detect ambient sound and convert the mechanical vibrations of the diaphragm 111 induced by the ambient sound to electric power. In some instances, the portable electronic device may include a pair of diaphragms one for generating sound and the other for generating tactile and generally inaudible vibrations.

FIG. 5 shows another example according to the present disclosure. The portable electronic device 10', a portion of which is schematically illustrated in FIG. 5, may include a housing 112 and piezo actuated vibrator assembly 114'. The piezo actuated vibrator assembly 114' may be implemented in a dual diaphragm configuration as will be described. The piezo actuated vibrator assembly 114' may include a first diaphragm 111' which may be used to produce tactile vibrations 120 while a second diaphragm 135 may be used to produce audible vibrations 140. In this example, the first diaphragm may be referred to as a tactile diaphragm and the second diaphragm may be referred to as an audio diaphragm based on the functionality which they may be configured to perform. The piezo actuated vibrator assembly 114' may include a piezoelectric element 116, which may be implemented according to any of the examples herein. The piezoelectric element 116 may be disposed between the first and second diaphragms 111', 135, and may by coupled to opposing sides of the first and second diaphragms 111',135 using a pair of connectors 121 and 121'.

In the example in FIG. 5, the first and second diaphragms 111', 135 are arranged such that they are opposite and spaced apart from each other. The piezo actuated vibrator assembly 114' may be arranged such that the first diaphragm 111' (e.g., tactile diaphragm) is an external diaphragm configured for placement against the user's skin, while the second diaphragm 135 (e.g., audio diaphragm) is an internal diaphragm, which may be partially or fully enclosed within the housing 112 of the portable electronic device 10'. The audio diaphragm may be acoustically coupled to a sound port provided through the enclosure for delivering sound generated by the audio diaphragm to the ambiance. In some examples a duct (not shown) may be provided around the internal audio diaphragm and used to acoustically couple the audio diaphragm with the sound port for directing sound waves through the interior of the electronic device and towards the exterior of the device. In other examples, the audio diaphragm may be exposed to the exterior similar to the tactile diaphragm.

In a similar manner to the example in FIG. 4, the first and second diaphragms 111', 135 may be coupled to a portion of the housing 113 which may be thicker and/or made of a different material than first and second diaphragms 111', 135. In some examples, the same material may be used for both the housing and diaphragms however they may differ in thickness as depicted in FIG. 2. The first and second diaphragms, 111', 135 respectively, may have different thicknesses as may be suitable for generating vibrations of a particular frequency and/or amplitude. For example, the tactile diaphragm may be thicker than the audio diaphragm, so as to enable the audio diaphragm to vibrate at higher frequencies than the tactile diaphragm when subjected to a force of the same magnitude.

Figure 6A:
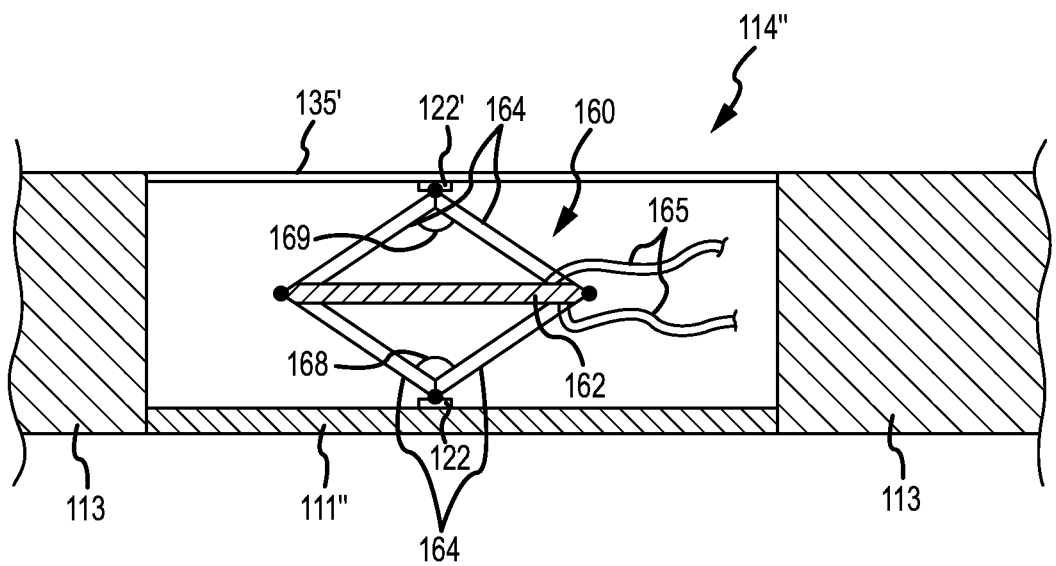
FIGS. 6A and 6B are schematic illustrations of piezo actuators according to other examples of the present disclosure.

As mentioned above, it may be desirable in some instances to increase the stroke of the piezo actuator (e.g., piezoelectric element 116). An amplification of the stroke through the use of flexures and/or linkages so as to obtain mechanical advantage may be used. A piezo actuator 160 with an amplified stroke may be implemented using rigid linking members 164 and an active piezo member 162 according to one example, as depicted in FIG. 6A, which shows a schematic illustration of a dual-diaphragm assembly. The first and second diaphragms 111″ and 135′ may be provided across an opening of the housing 113, and configured according to any of the examples herein. The piezo actuator 160 may be disposed between the diaphragms and coupled to opposing surfaces of the diaphragms using connectors 122, 122′. The piezo actuator 160 may include the active element, which may be made of a piezoelectric material which is configured to elongate upon being energized. Each end of the piezo actuator 160 may be coupled to two linking members, which may be pivotally coupled together. The linkage assembly 163 may be hingedly coupled to opposing surfaces of the diaphragms 111″, 135′. Voltage may be applied to the piezo active element 162 via electrical leads 165 causing the piezo active element 162 to elongate. The elongation of the piezo active element 162 may cause the angles 168, 169 between the linking arms at each of the connections to increase thereby causing the diaphragms 111″, 135′ to deflect towards each other. In a next instance, contraction of the piezo active element 162 may cause the angles 168, 169 to decrease and the connection points to deflect away from each other. Repetitive elongation/contraction of the piezo active element would thus cause the diaphragms to vibrate. As will be understood, a piezo actuator of this kind may be implemented regardless of whether or not two diaphragms are used. In some examples, the top portion of the linkage assembly may be coupled to a supporting member which may be substantially stiffer than the diaphragm. In this manner, the support member may not be configured to deflections but may instead be used as a spring board against which the deflections of the actuator may be transmitted to the diaphragm 111″.

Figure 6B:
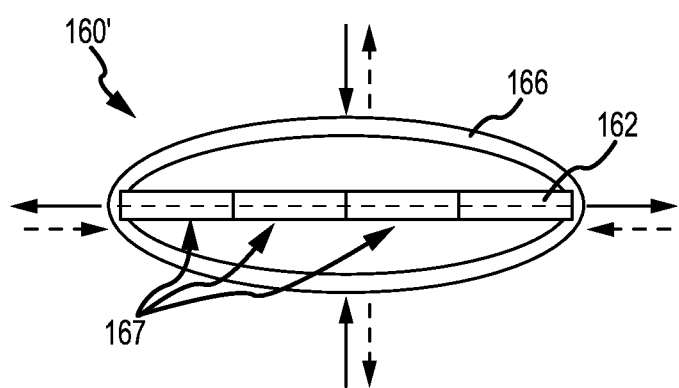

Another variant of an amplified piezo actuator 160′ is shown in FIG. 6B. In this example, the linkage assembly 166 is elliptical in shape instead of diamond-shaped as in the previous example. In an analogous manner to the example in FIG. 6A, an elongation or contraction of the piezo active element 162′ (e.g., along the major axis of the ellipse) may cause contraction or elongation of the minor axis of the elliptic linkage assembly, respectively. In the present example, the piezo active element 162 is implemented as a "extender" type stack (e.g., a stack of PZT bars 167 arranged adjacent to each other along their longitudinal axes.) As previously described, this arrangement may allow for increased applied force, control, and/or reliability of the piezo actuator 160′.

Another technique for amplifying the stroke of the piezo actuator may be to use one or more lever arms, as shown in FIG. 7. In that example, the piezo active element 162″ may be suspended over the diaphragm 111‴ using a pair of lever arms 171, 173, which may be rigidly mounted to both the piezo active element 162″ and the diaphragm 111‴. Ends of the piezo active element 162″ may be nominally supported using a low damping spring assembly or a low friction roller or other type of bearings assembly to allow the ends to freely move. Elongation and contraction of the ends of the piezo element 162″ may cause a bending moment to be applied at each joint between the lever arms and the diaphragm causing the diaphragm to deflect accordingly. Different patterns of deflection may be possible according to the examples described herein. The contact surface 115′ of the present example may be curved as shown in FIG. 7, or it may be generally flat as described with references to other examples herein. While two lever arms are used in the example in FIG. 7, in other instances one lever arm may instead be used. For example, the piezo active element 162″ may be cantilevered from the housing 113′ and a single lever arm may be used to couple the free end of the piezo active element 162″ to the diaphragm 111‴. Many other variations may be implemented and will be appreciated in light of this disclosure.

FIG. 8 shows another example according to the present disclosure. In the example in FIG. 8, a piezo actuated diaphragm 101 is coupled around its perimeter to a housing 112′ of the electronic device 10″. One or more linear piezo actuators 103 are coupled generally perpendicularly to the diaphragm 101. The linear piezo actuators 103 may be generally cylindrical or rectangular PZT bars, which may be fixedly attached to the diaphragm 101 and a support beam 107 opposite the diaphragm. A cavity 105 may be defined between opposing surfaces of the diaphragm 101 and the support beam 107, which cavity may be filled or may remain emptily. As will be understood, the linear piezo actuators 103 may be configured to elongate or contract along their longitudinal direction (e.g., as indicated by the arrows 108) upon the application of voltage. As will be further understood, the elongation and contraction of the one or more piezo actuators may cause the diaphragm to vibrate. All or some of the piezo actuators may be driven simultaneously and/or they may be driven according to virtually any pattern to producing tactile vibrations (e.g., tapping sensations) at certain portions or along the entire surface of the diaphragm 101.

According to other examples of the present disclosure, the piezoelectric element may be integral with the housing. The piezo ceramic portion may be fused or bonded to a portion of the housing such that it is indistinguishable from other (non-piezo) portions of the housing. In some examples, the housing itself or portions of the housing may be made of a piezo ceramic material. In such examples, the piezo ceramic housing or the piezo ceramic portion of the housing may be configured to generate vibrations, which may be perceived tactually or audibly by the user.

Figure 9:
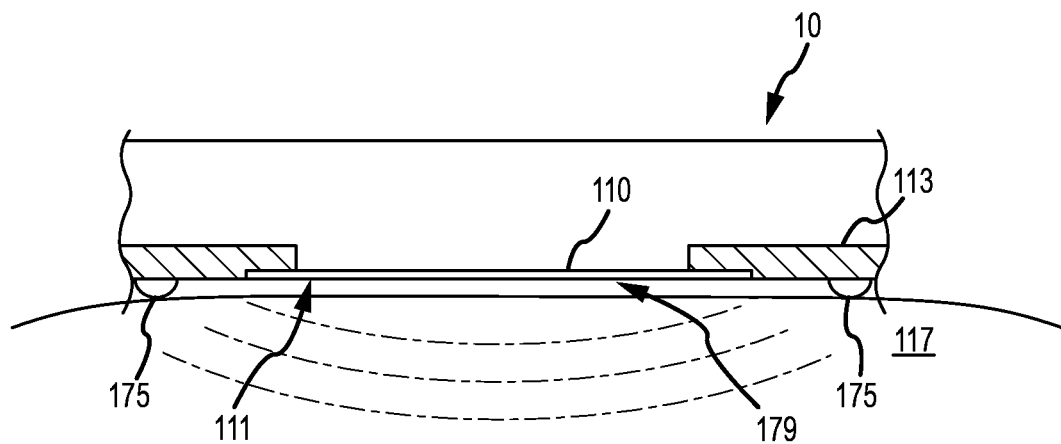
FIG. 9 is an example of a portable electronic device including an integrated piezo diaphragm.

FIG. 9 shows an example according to the present disclosure, in which the piezo element and diaphragm are integrated into a piezo actuated component 110, which may be mounted flush with the housing so as to be perceived as integral with the housing. The portable electronic device 10 in this example includes a housing 113 which encloses the internal electronics (not shown) of the device 10. The housing may include a piezo actuated component 110 incorporating providing the functionality of both the piezo actuator and diaphragm. The piezo actuated component 110 may be implemented by embedding the piezo material within the diaphragm and/or by making the diaphragm from a piezo material such that it may be directly vibrated when current applied thereto. As previously described, in some examples, the piezo actuated component may function as a tactile vibrator or it may function as a speaker (e.g., a sound generating component). In the present example, the housing 113 is provided in a spaced apart configuration with respect to the user's skin to allow for better generation of sound. The housing 113 may be provided with spacers 175 to allow the exterior surface of the piezo actuated component 110 to be maintained in a spaced apart position.

Figure 10:
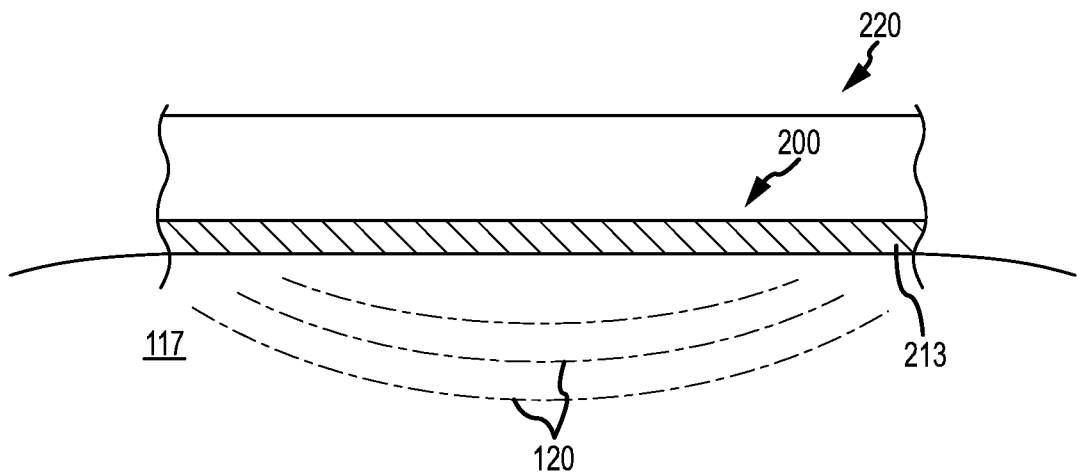
FIG. 10 is an example of a portable electronic device including a piezo ceramic housing.

According to yet other examples, piezo actuated vibrators for portable electronic devices may be implemented by using a piezo ceramic or piezocomposite housing, as will be further described with reference to FIGS. 10-11. According to some examples of the present disclosure, the housing 213 of a portable electronic device 220 may itself include piezoelectric material, for example the housing may be constructed from a piezoelectric ceramic material which is shaped as appropriate for the particular application. Certain portions of the piezoelectric housing 200 may be insulated from other portions such that individual portions may be independently controlled and/or driven to vibrate. Electrical leads and driver circuitry may be provided to the one or more portions of piezoelectric ceramic material incorporated into the housing. In some examples, the housing may be made of a ceramic, a plastic, or a composite material. Piezoelectric material may be integrated into the housing, for example by incorporating one or more layers of a piezoelectric crystal or ceramic into the structure of the housing. A composite laminate including layers of piezoelectric and non-piezo materials may be formed by conventional composite fabrication techniques.

Piezoelectric composite structures (e.g., piezocomposites) may be used according to some examples of the present disclosure. A piezocomposites according to the present disclosure may include a matrix or bulk material which is non-piezo material. The matrix or bulk material may be a metal, a polymer such as resin or polycarbonate acrylonitrile butadiene styrene (PC/ABS) plastic, or a non-piezo ceramic material. One or more layers, strands, or particles of piezo material layer may be integrated within the base material. Leads for supplying or harvesting electrical energy may extend from the piezo material to a surface of the piezocomposites housing. Piezocomposites according to the present disclosure may be formed using conventional composite manufacturing techniques, including laminating and/or injection molding techniques. Piezocomposites may be injection molded or laminated to virtually any shape or configuration. Unlike traditional monolithic piezoelectric ceramics (e.g., a bar or a thin wafer of PZT), piezocomposite structures may be particularly suitable for applications within curved structures due to the ability to shape piezocomposites to virtually any shape.

Figure 11A:
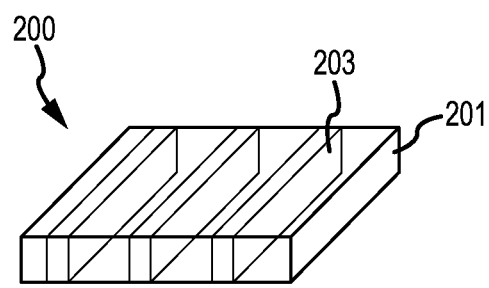
FIG. 11A-C show examples of piezocomposite configurations for a piezo actuated housing of a portable electronic device according to the present disclosure.
Figure 11B:
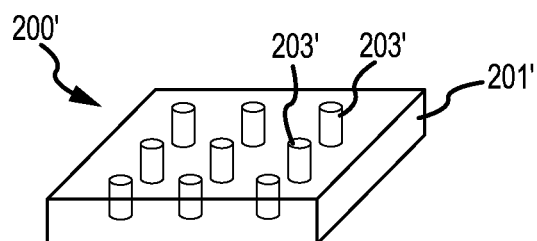
Figure 11C:
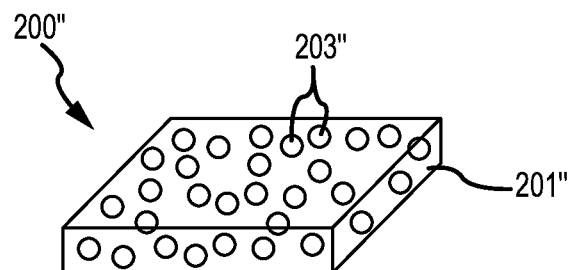

According to some examples, longitudinal bands 203 of piezo material may be incorporated within the bulk material 201 of the housing piezo ceramic housing 200 (see FIG. 11A). In some examples, the bands 203 may be generally aligned and/or constant in thickness along their length. In other examples, the bands 203 may vary in thickness or orientation along their length. In yet other examples, the housing 113 of the electronic device 10 may naturally deflect (e.g., stretch, or bend) by a certain amount. In such examples, corrugated bands of piezo material, for example bands made of a piezo polymer, may be used to minimize damage, for example cracking, of the piezo material when the housing experiences larger deflections. Other configurations or shapes of the piezo material may be used to achieve a deflection pattern. Concentric annular strips of piezo material may be arranged in a pattern to form a circular piezocomposite diaphragm. According to further examples, piezo rods 203' may be arranged along the transverse direction within the bulk material 201' and may be used as linear actuators to cause tactile stimulation to the user through the housing 200', as shown in FIG. 11B. The rods may be arranged in an array, they may be clustered, or arranged in virtually any other pattern. In yet other examples, discrete beads of piezo material 203" may be dispersed in a random or orderly pattern throughout the bulk material 201" of the housing 200" (see FIG. 11C), which beads 203" may be effectively coupled to driver to achieve virtually any vibration pattern.

The piezoelectric element of portable electronic devices according to this disclosure may be configured to conversely harvest strain in the material of the housing. For example, when worn, a portable electronic device may be secured against the skin of the wearer. The piezoelectric element may be configured to sense deflections of varying magnitude, for example micro deflections caused due to muscle contraction and/or expansions of the body part to which the product is secured. The piezoelectric element may be further configured to sense acoustic energy from the ambiance and/or from the user's body (e.g., a pulse or heartbeat of the person). The piezoelectric element may be operatively coupled to circuitry to record the event (e.g., muscle spasm, heartbeat, or other biometric information) and may be further configured to harvest the electrical energy corresponding to the sensed mechanical stress.

Although embodiments described herein have generally referenced piezoelectric elements, it should be appreciated that certain other materials, such as electroactive polymers, electromagnetically driven materials, and other similar materials may be used in lieu of piezoelectrics. In some embodiments, a motion or force that is generally planar to a device/housing surface or a user's skin may be induced instead of a perpendicular motion or force.

Numerous technical advantages may be achieved according to the present examples. One advantage may be ability to further reduce the size of portable electronics, and in some examples use the housing of the portable device to produce sound, audible vibrations and other tactile feedback. Two generally separate electro-mechanical systems may thus be combined into a single system (e.g., by using the housing of the device as a speaker and a vibrator), which may further reduce the overall size and/or power consumption of the device. Moreover, using a piezoelectric actuator for a vibrator obviates the need for a motor-based vibrator, reducing the number of moving components and potentially the complexity of the electromechanical systems therewithin. Notably, the overall thickness of a product may be reduced, as motor-type vibrators tend to be larger and heavier than a piezo actuated vibrators. Further, by incorporating the piezoelectric material within the housing (e.g., in the case of an integral piezoceramic housing), the thickness of the device may be further reduced. In some examples, the piezo actuator assembly may be configured to reverse the piezoeffect of the piezoelectric material, such that the piezo actuator may operate as a piezo sensor generating a change in electrical potential in response to detected deflections. In these embodiments, the piezoelectric element may be accordingly configured to generate electrical power responsive to detected movement of the diaphragm. In other examples, the piezo sensor may be used to measure biometric information related to the user, for example the pulse or heartbeat of the user. Other potential uses for the piezo sensor incorporated in a housing of the portable device may be possible and/or depending on the particular device and placement.

Some of the advantages of the examples described herein may include the ability to generate very precise movements while being very compact and having low energy consumption. Furthermore, piezoelectric actuators generally have quick response times and generally do not have EMI (electromagnetic interference) which can be particularly significant in the case of using a piezo actuator in a compact portable electronic device. While certain example advantages have been described, other advantages of the examples herein may be appreciated, and some embodiments may or may not offer the same or any advantages over existing systems.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A portable electronic device comprising:
a housing defining an exterior surface of the portable electronic device; and
a vibrator assembly, including:
a piezoelectric element coupled to the housing and having an axis of elongation that is substantially parallel to the exterior surface; and
a driver circuit positioned in the housing and configured to apply a signal to the piezoelectric element, wherein:
applying the signal to the piezoelectric element changes a dimension along the axis of elongation of the piezoelectric element, thereby bending the piezoelectric element and deflecting at least a portion of the exterior surface in a direction transverse to the axis of elongation of the piezoelectric element to selectively produce at least one of a tactile output or an audio output.

2. The portable electronic device of claim 1, wherein:
the vibrator assembly further includes a first diaphragm coupled to the housing and a second diaphragm opposite and spaced apart from the first diaphragm; and
the piezoelectric element is spaced apart from and coupled to the first and the second diaphragms and configured to cause the first and the second diaphragms to vibrate simultaneously.

3. The portable electronic device of claim 2, wherein the first diaphragm has a first thickness and the second diaphragm has a second thickness different than the first thickness.

4. The portable electronic device of claim 2, wherein the first diaphragm and the second diaphragm are configured to produce first and second vibrations, respectively, in response to a load applied by the piezoelectric element, wherein a frequency or magnitude of the first vibrations is different than a frequency or magnitude of the second vibrations.

5. The portable electronic device of claim 2, wherein vibrations of at least one of the first or the second diaphragms are inaudible to a user of the portable electronic device.

6. The portable electronic device of claim 2, wherein at least one of the first or the second diaphragms is configured to amplify a vibration of the other one of the first or the second diaphragms.

7. The portable electronic device of claim 2, wherein at least one of the first or the second diaphragms is enclosed within the housing.

8. The portable electronic device of claim 7, wherein the at least one of the first or the second diaphragms enclosed within the housing is configured to generate sound.

9. The portable electronic device of claim 1, further comprising a strap for securing the portable electronic device to a body part of a user.

10. The portable electronic device of claim 1, wherein the vibrator assembly further includes a linkage assembly for amplifying a stroke of the piezoelectric element.

11. The portable electronic device of claim 1, wherein a shape of the piezoelectric element corresponds to a shape of an existing feature of the housing.

12. The portable electronic device of claim 1, further comprising a sound generating component configured to provide a noise cancellation signal for canceling sound produced by the piezoelectric element.

13. The portable electronic device of claim 1, wherein the portable electronic device is configured to be attached to a body part of a user, and wherein the vibrator assembly is further configured to detect a pulse or a heartbeat of the user.

14. The portable electronic device of claim 1, wherein the portable electronic device is configured to be attached to a body part of a user, the housing further comprising exterior features configured to maintain a gap between the exterior surface and the body part of the user when the portable electronic device is worn by the user.

15. The portable electronic device of claim 1, wherein the housing is made from a ceramic material, at least a portion of said ceramic material being piezoceramic material that forms the piezoelectric element.

16. The portable electronic device of 19, wherein the exterior surface is curved and configured for placement against skin of the user.

17. The portable electronic device of claim 1, wherein:
the housing further defines an interior surface; and
the piezoelectric element is embedded between at least a portion of the interior surface of the housing and the exterior surface of the housing, the piezoelectric element being arranged such that the axis of elongation of the piezoelectric element is parallel to the interior surface of the housing.

18. A portable electronic device comprising:
a housing defining an exterior surface of the portable electronic device and comprising a piezoelectric portion at least partially formed of a piezoelectric material and having an axis of elongation that is substantially parallel to the exterior surface; and
a driver circuit positioned in the housing and configured to apply a voltage to the piezoelectric portion, thereby causing the piezoelectric portion of the housing to deflect in a direction transverse to the exterior surface to produce one or both of a tactile output and an audio output.

19. The portable electronic device of claim 18, wherein the housing further comprises an additional portion insulated from the piezoelectric portion.

20. The portable electronic device of claim 18, wherein the piezoelectric material is a piezocomposite.

21. The portable electronic device of claim 18, wherein:
the piezoelectric portion comprises one or more piezoelectric layers; and
the housing further comprises one or more non-piezo layers.

* * * * *